United States Patent [19]

Jang

[11] Patent Number: 5,263,932
[45] Date of Patent: Nov. 23, 1993

[54] BAILOUT CATHETER FOR FIXED WIRE ANGIOPLASTY

[76] Inventor: G. David Jang, 636 Golden West Dr., Redlands, Calif. 92373

[21] Appl. No.: 865,975

[22] Filed: Apr. 9, 1992

[51] Int. Cl.$^5$ ............................................. A61M 29/00
[52] U.S. Cl. ..................................... 604/96; 604/102; 604/160; 606/194
[58] Field of Search ..................... 604/49, 53, 95, 96, 604/101, 102, 160; 606/192, 194

[56] References Cited

U.S. PATENT DOCUMENTS

| | | |
|---|---|---|
| Re. 31,855 | 3/1985 | Osborne . |
| 3,297,030 | 1/1967 | Czorny et al. . |
| 3,550,591 | 12/1970 | MacGregor . |
| 3,682,173 | 8/1972 | Center . |
| 3,853,130 | 12/1974 | Sheridan . |
| 4,054,136 | 10/1977 | von Zeppelin . |
| 4,079,738 | 3/1978 | Dunn et al. . |
| 4,175,564 | 11/1979 | Kwak . |
| 4,411,055 | 10/1983 | Simpson et al. . |
| 4,411,654 | 10/1983 | Boarini et al. . |
| 4,569,347 | 2/1986 | Frisbie . |
| 4,573,470 | 3/1986 | Samson et al. . |
| 4,581,017 | 4/1986 | Sahota . |
| 4,585,013 | 4/1986 | Harris . |
| 4,619,644 | 10/1986 | Scott . |
| 4,631,059 | 12/1986 | Wolvek et al. . |
| 4,705,507 | 11/1987 | Boyles . |
| 4,738,666 | 4/1988 | Fuqua . |
| 4,747,833 | 5/1988 | Kousai et al. . |
| 4,748,982 | 6/1988 | Horzewski et al. . |
| 4,762,129 | 8/1988 | Bonzel . |
| 4,771,777 | 9/1988 | Horzewski et al. . |
| 4,813,930 | 3/1989 | Elliott . |
| 4,888,000 | 12/1989 | McQuilkin et al. . |
| 4,944,745 | 7/1990 | Sogard et al. . |
| 4,947,964 | 8/1990 | Shockey et al. . |
| 4,958,634 | 9/1990 | Jang .............................. 604/96 |
| 4,983,167 | 1/1991 | Sahota .......................... 604/96 |
| 4,988,356 | 1/1991 | Crittenden et al. . |
| 4,997,424 | 3/1991 | Little . |
| 5,040,548 | 8/1991 | Yock . |
| 5,046,503 | 9/1991 | Schneiderman . |
| 5,061,273 | 10/1991 | Yock . |
| 5,102,403 | 4/1992 | Alt . |
| 5,135,535 | 8/1992 | Kramer ........................ 604/160 |

FOREIGN PATENT DOCUMENTS

8203558 10/1982 World Int. Prop. O. .

Primary Examiner—John D. Yasko
Assistant Examiner—Anthony Gutowski
Attorney, Agent, or Firm—Knobbe, Martens, Olson & Bear

[57] ABSTRACT

An angioplasty catheter, comprising a catheter shaft having a proximal end and a distal end, with a balloon inflation lumen extending therethrough, a fixed, steerable torquewire extending through at least a portion of the shaft and out of the distal end thereof, an angioplasty balloon on the distal end of the catheter operatively communicating with the balloon inflation lumen for inflation and deflation of the balloon, wherein the proximal end of the balloon is attached to the distal end of the catheter shaft and the distal end of the balloon is attached to the torquewire, and a bailout lumen extending along the catheter shaft from a point ordinarily outside the patient during use to a point proximal of the balloon and normally inside the patient during such use, the bailout lumen adapted to receive a removable guidewire and having an outer wall, with the outer wall preferably including a means such as a longitudinally extending slit for laterally removing the catheter from the patient and off of the guidewire while maintaining the position of the guidewire in the patient, and optionally including a side port through the outer wall of the bailout lumen through which a guidewire can be inserted. Methods for using the catheter are also disclosed.

28 Claims, 10 Drawing Sheets

BAILOUT CATHETER FOR FIXED WIRE ANGIOPLASTY

BACKGROUND OF THE INVENTION

Percutaneous transluminal coronary angioplasty (PTCA) has emerged as the major viable present alternative to bypass surgery for revascularization of stenotic and occluded coronary arteries. Although transluminal angioplasty has application in peripheral artery disease, it is most widely used in the treatment of coronary artery disease. Unlike bypass surgery, percutaneous angioplasty does not require general anesthesia, cutting of the chest wall, extracorporeal perfusion, or transfusion of blood. Percutaneous coronary angioplasty is not only less invasive and less traumatic to the patient, it is also less expensive because the angioplasty patient will have a shorter hospital stay and shorter post-procedure recovery time.

Percutaneous transluminal angioplasty is performed by making a skin puncture with a specially-designed needle in one of the groins, and then introducing a guiding catheter into the aorta and coronary artery orifice. A smaller caliber catheter with a built-in inflatable and deflatable balloon of predetermined size and diameter is passed through the guiding catheter which is positioned in the orifice of a target artery. This balloon catheter (with the balloon totally deflated by negative pressure) is advanced inside the target coronary artery toward the point of obstruction in need for dilation.

The guidewire plays an essential role in leading the balloon catheter to the target coronary artery in safe and non-traumatic fashion. With the balloon portion of the catheter properly positioned inside the obstructed arterial segment, under X-ray fluoroscopic observation, the balloon is inflated by injecting contrast media mixed with saline at a pressure sufficient to overcome the resistance of the arteriosclerotic plaque of the obstructed segment.

By inflating the balloon in the stenosis multiple times over a period of between 10-30 seconds and one or two minutes (allowing blood flow between inflations), the desired dilation of the obstructed arterial segment can be achieved. After dilation, the guiding catheter, the balloon catheter (with the balloon completely deflated by negative pressure) and the guidewire are withdrawn from the artery and the patient, and the procedure is successfully terminated.

The size and diameter of the balloon to be used in transluminal angioplasty should be approximately matched to the size and native diameter of the obstructed arterial segment to be dilated. If the balloon size and diameter is smaller than the native artery, the results of balloon angioplasty are suboptimal, requiring a second dilation with a larger-sized balloon. If the balloon size is too large for the native artery, complications may occur due to arterial wall damage.

Conventional over-the-wire angioplasty catheters, with a guidewire lumen extending their entire length, permit simple guidewire exchange. Another type of angioplasty catheter has a guidewire permanently attached to the catheter at the distal end. This fixed wire, low profile catheter can be manufactured with a small overall diameter since there is no separate guidewire lumen. The guidewire in this type of catheter is referred to herein as a torquewire. Fixed wire catheters, although being preferred by many physicians because of their small diameter, have no provision for rapid replacement of either the torquewire or catheter. If, for example, balloon replacement becomes necessary once the catheter is positioned at a stenosis, the entire catheter must be removed and the balloon catheter reinserted into the artery, starting the procedure over again. Similarly, if the torquewire tip must be reshaped or replaced, the only option is removal of the entire catheter. Currently available fixed wire catheters do not have the benefit of rapid replacement.

Emergency situations can also arise during or after angioplasty. For instance, after balloon dilation, the vessel wall may collapse, requiring immediate insertion of a perfusion catheter. Accordingly, there is a need for an angioplasty catheter which retains the low distal-end profile of a fixed wire catheter while still providing the ability for rapid-exchange.

SUMMARY OF THE INVENTION

In accordance with one aspect of the invention, there is provided an angioplasty catheter, comprising a catheter shaft having a proximal end and a distal end, with a balloon inflation lumen extending therethrough, a fixed, steerable torquewire extending through at least a portion of the shaft and out of the distal end thereof, an angioplasty balloon on the distal end of the catheter operatively communicating with the balloon inflation lumen for inflation and deflation of the balloon, wherein the proximal end of the balloon is attached to the distal end of the catheter shaft and the distal end of the balloon is attached to the torquewire, and a bailout lumen extending along the catheter shaft from a point ordinarily outside the patient during use to a point proximal of the balloon and normally inside the patient during such use, the bailout lumen adapted to receive a removable guidewire and having an outer wall. In one preferred embodiment, the outer wall is adapted to at least partially collapse into the bailout lumen when the bailout lumen is empty. In a first variation, only a distal portion of the outer wall of the bailout lumen is adapted to collapse when empty. Optionally, a proximal portion of the outer wall is adapted to remain open when empty and is thicker than the collapsible distal portion thereof. In another embodiment, the bailout lumen has a proximal opening at its proximal end and a distal opening at its distal end, the proximal opening is within about 30 cm of the proximal end of the catheter shaft and the distal opening is within about 30 cm of the balloon.

Another preferred embodiment includes a side port extending through the outer wall of the bailout lumen, the side port located between the proximal and distal ends of the bailout lumen and adapted to permit a guidewire to extend therethrough to pass through a distal portion of the bailout lumen. Preferably, the side port is located at a point normally inside a patient when the catheter is in use. The side port is advantageously located within about 30 cm of the distal end of the bailout lumen.

In a particularly preferred embodiment, the fixed wire bailout catheter includes means for removing a guidewire laterally out of the bailout lumen. In one embodiment, the guidewire removing means is adapted to permit removal of the guidewire from the bailout lumen beginning at the proximal end of the bailout lumen and progressing distally to within no more than 30 cm of the balloon. The guidewire removing means may advantageously comprise means for providing an opening through the outer wall extending longitudinally along the outer wall, such as a slit extending longitudinally along at least 50% of the length of the outer wall; a weakened area adapted to open into a slit extending longitudinally along at least 50% of the length of the outer wall, optionally with an open slit extending distally from the proximal end of the outer wall to the weakened area; or a tear away strip forming at least a portion of the outer wall and adapted to tear away from the catheter and form an opening extending longitudinally along at least 50% of the length of the outer wall, which may advantageously be defined by two longitudinally extending parallel weakened areas of the outer wall. It is additionally contemplated that the tear away strip may be further defined by two parallel formed slits extending from the proximal end of the outer wall to the weakened areas. These weakened areas may include an embodiment where the outer wall is joined to the catheter shaft along two longitudinally-extending junctions, and the weakened areas comprise the junctions. When the outer wall has a side port extending therethrough, located between the proximal and distal ends of the bailout lumen and adapted to permit a guidewire to extend therethrough to pass through a portion of the bailout lumen, the means for providing an opening preferably extends distally along the outer wall to the side port.

Another aspect of the present invention is a method for performing bailout of a fixed wire angioplasty catheter, comprising: (a) advancing a first balloon catheter as defined above into a patient's vascular system, wherein the vascular system includes a stenosis, (b) advancing a guidewire through the bailout lumen of the first catheter and out of the distal end of the bailout lumen into a position in the patient's vascular system, (c) removing the first balloon catheter from the patient while maintaining the guidewire in the position in the vascular system, and (d) advancing a second catheter into the vascular system of the patient over the guidewire. The method may further comprise the steps after step (a) and before step (b) of inflating and deflating the balloon of the first catheter in the stenosis, then advancing the first catheter forward until the distal end of the bailout lumen is advanced to or through the stenosis, whereby step (b) results in the guidewire extending into the stenosis. The method may, alternatively, include a method wherein the guidewire is advanced into or through the stenosis in step (b), further comprising the step, after step (a) but before step (c), of inflating and deflating the angioplasty balloon of the first catheter in the stenosis with the guidewire extending through the stenosis. Also included is a method wherein the angioplasty balloon of the first balloon catheter is inflated and deflated in the stenosis prior to step (b), and the guidewire is advanced past the deflated balloon in the stenosis in step (b).

In accordance with another aspect of the invention, there is provided a method for performing balloon angioplasty, in bifurcation lesions, comprising: (a) advancing the balloon segment of a catheter as defined above into a first stenosis of the bifurcation in a patient's vascular system, (b) advancing a guidewire through the bailout lumen of the catheter and out of the distal end of the bailout lumen into a second stenosis of the bifurcation in the patient, and (c) inflating and deflating the balloon in the first stenosis. This method may further comprise the subsequent steps of (d) inserting the balloon into the second stenosis and the guidewire into the first stenosis, and (e) inflating and deflating the balloon in the second stenosis. It may also include the subsequent step of removing the first balloon catheter over the guidewire, and inserting a second catheter into the vessel over the guidewire.

In yet another embodiment, the invention includes a method for performing bailout of a fixed wire angioplasty catheter, comprising (a) advancing a first balloon catheter as defined above into a patient's vascular system, wherein the vascular system includes a stenosis, (b) advancing a guidewire through the bailout lumen of the first catheter and out of the distal end of the bailout lumen into a position in a stenosis in the patient's vascular system, (c) advancing the first balloon catheter into the stenosis and inflating and deflating the balloon to dilate the stenosis while the guidewire is in position in the stenosis, and (d) removing the first balloon catheter from the patient while maintaining the guidewire in position in the stenosis. This method may also include the step (e) of advancing a second catheter into the vascular system of the patient over the guidewire.

BRIEF DESCRIPTION OF THE DRAWINGS

FIG. 11, panels a–d, illustrate a clinical angioplasty procedure using the fixed-wire, bailout features.

FIG. 12, panels a–d, illustrate an alternative clinical angioplasty procedure using the inventive bailout catheter.

FIG. 13, panels a–d, illustrate another clinical angioplasty procedure using the inventive bailout catheter.

FIG. 14, panels a–h, illustrate a clinical angioplasty procedure at a vessel bifurcation on dual stenoses using the inventive features of the catheter.

DETAILED DESCRIPTION

The angioplasty catheter of the present invention combines the advantages of a low profile, fixed wire catheter with the benefits of rapid guidewire and catheter exchange. Specifically, the present invention provides a low profile, fixed wire catheter containing an exterior, preferably collapsible, bailout lumen. The bailout lumen is a longitudinal receptacle or channel running distally from the proximal end of the catheter shaft to a point just proximal of the angioplasty balloon. A guidewire can be inserted into this bailout lumen in the event a catheter exchange becomes necessary during an angioplasty procedure.

During such an exchange, a guidewire is inserted into the proximal end of the bailout lumen so that it fully traverses the lumen and protrudes a distance from the distal end. The fixed wire catheter can thereafter be removed proximally over the guidewire while keeping the guidewire tip immobile at, or distal to, the site of stenosis. A new catheter can then be rapidly and safely inserted to the same stenotic region by advancement over the inserted guidewire. The new catheter could be a perfusion catheter, a conventional over the wire catheter, a rapid exchange catheter, another fixed wire catheter having a bailout lumen, or any other device capable of being inserted over a guidewire. The combination of a low profile design and bailout lumen provides a vast improvement over currently available fixed wire angioplasty catheters.

Figure 1:
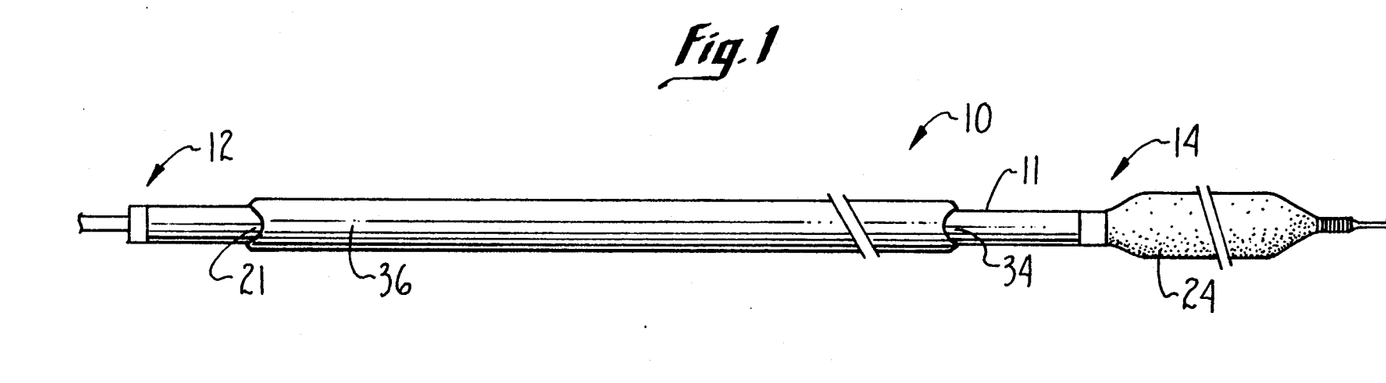
FIG. 1 is an on-face ventral view of one embodiment of the present bailout catheter.

Specifically, referring to FIG. 1, the fixed wire bailout catheter 10 of the present invention comprises a longitudinally extending catheter shaft 11 with a proximal end 12 and distal end 14. The catheter shaft 11 is preferably made of any suitable conventional polymer material, such as polyethylene, polyvinylchloride, polyethylene terephathalate, or other suitable materials. The catheter 10 preferably has an outer diameter of between F 3.0 and F 3.5 with the most preferable diameter being under F 3.5.

Overlaying one portion of the catheter shaft 11 is a bailout lumen wall 36 which forms the exterior portion of a bailout lumen 20 (not shown). The proximal end of the bailout lumen wall 36 defines an entry point 21 to the lumen 20. The distal edge of the bailout wall 36 defines the distal exit point 34 of the bailout lumen 20. Attached to the distal end of the catheter shaft 11 is an angioplasty balloon 24.

The balloon 24 is usually a generally cylindrical angioplasty balloon, and can be made in accordance with conventional techniques for fabricating angioplasty balloons. Preferably, it is either blown from the distal end 14 of the catheter shaft 11, or is blown or formed of a separate piece of material which is bonded to the distal end 14 of the catheter shaft 11. The balloon 24 may advantageously be formed of relatively inelastic polymer material, such as polyethylene, polypropylene, polyvinylchloride, polyethylene terephthalate, or similar materials.

Figure 2:
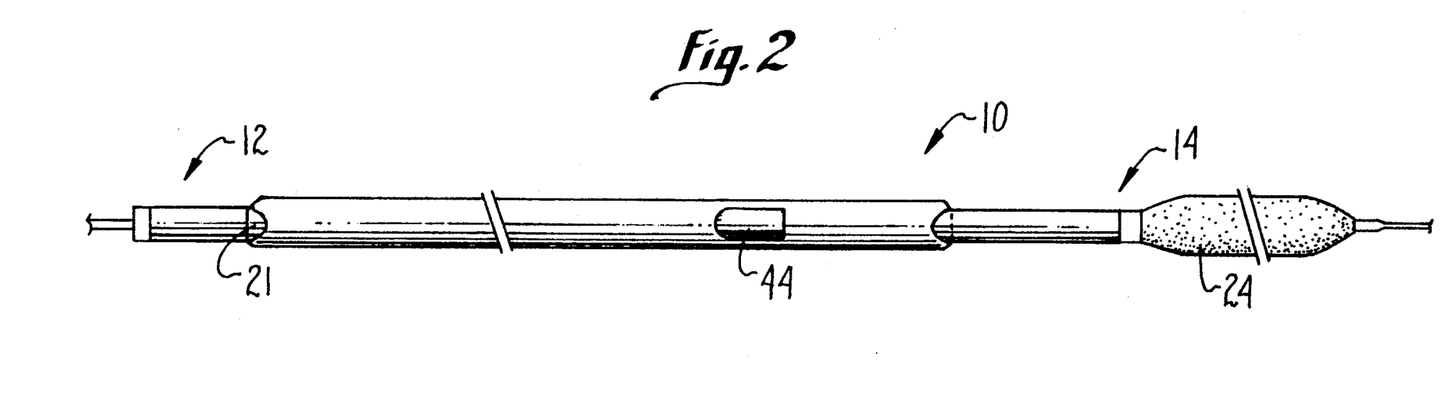
FIG. 2 is an on-face ventral view of one embodiment of the present bailout catheter incorporating a distal side port.

Referring now to FIG. 2, one preferred embodiment of the catheter 10 contains a distal side port 44 formed from the bailout lumen wall 36. The side port 44 is located distally of the proximal opening 21 of the bailout lumen, at a point normally inside of the patient when the catheter is properly in place for performance of an angioplasty procedure. Preferably, the side port 44 is located proximally of the balloon 24 and within 80 cm, preferably 60 cm, and more preferably within about 40 cm of the balloon 24. It is further contemplated that the side port can be used as a perfusion port, permitting the catheter 10 to be used as a perfusion catheter. In this embodiment, the side port 44 is preferably located relatively close to the balloon, perhaps within about 5 cm, and the bailout lumen extends to within about 1 or 2 cm of the balloon. The side port 44 need not be adapted to receive a guidewire when its function is solely as a perfusion port, and could in that event comprise multiple smaller openings into the bailout lumen. In using the catheter 10 as a perfusion catheter, the catheter is advanced so that the side port 44 is on one side of a lesion and the distal point 34 is located on the other side of the lesion. This permits blood to enter the side port 44 and exit the distal point 34, thereby traversing the lesion. The bailout lumen is preferably non-collapsible when used as a perfusion catheter.

Figure 3:
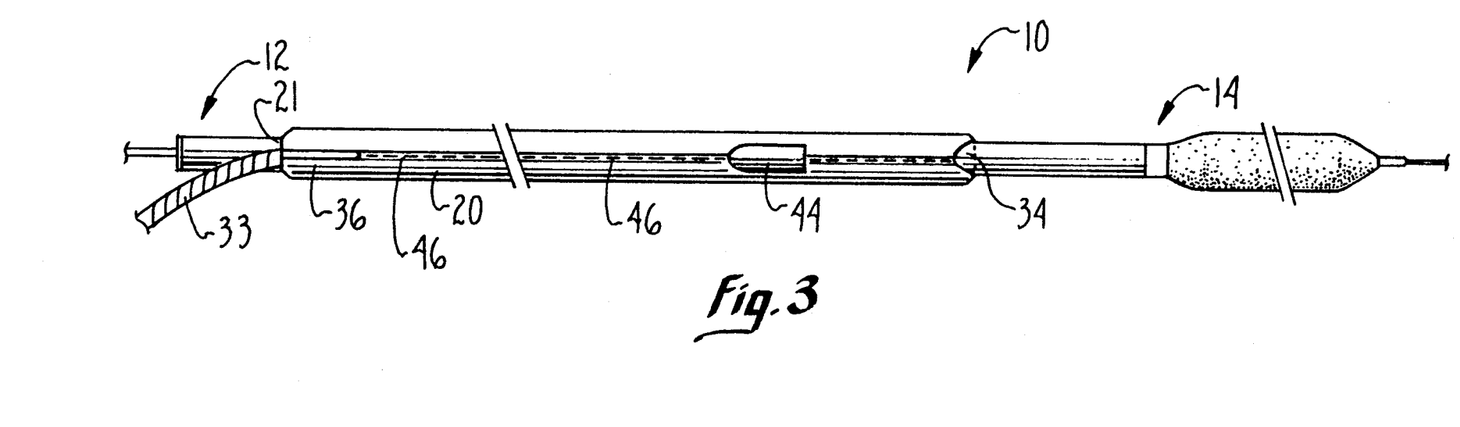
FIG. 3 is an on-face ventral view of one embodiment of the present bailout catheter incorporating a distal side port and a longitudinal guidewire removing means.

The catheter 10 of the present invention can advantageously be provided with a removal means 46 for removing a guidewire 33 out of the bailout lumen 20 through the outside wall 36 as shown in FIG. 3. If the catheter shaft 11 or the guidewire 33 is considered to extend in a longitudinal or axial direction, this guidewire movement out of the bailout lumen 20 can be considered as a lateral, sideways, radial, or transverse motion. The guidewire removing means 46 is adapted to provide a slit or other longitudinal opening through the outside wall 36 of the bailout lumen 20 through which the guidewire may be removed laterally from inside the bailout lumen 20. The guidewire removing means 46 may be an actual slit cut entirely through the side wall 36 of the bailout lumen 20. Alternatively, it may be an inchoate slit or perforated or weakened line. The guidewire removing means 46 may be cut entirely through the outside wall 36 of the bailout lumen 20, or only in certain sections, leaving other sections at least partially intact, to form a type of perforated line. The removal means 46 may be formed of the same material or a different material than the remainder of the catheter shaft 1 and even of a different material than the adjacent portions of the outside wall 36 of the bailout lumen 20. Combinations of fully formed slits and weakened areas or inchoate slits are also contemplated, such as having an inchoate slit in portions of the catheter normally outside the patient during use (eliminating backbleeding through the slit) and a fully formed slit in a portion of the catheter normally inside the patient during use. Although not the most preferred embodiment, one embodiment of FIG. 3 would contain the guidewire removal means 46 but without a distal side port 44. In one embodiment, the removal means extends substantially the entire distance from the guidewire lumen entrance 21 to the distal point 34.

One advantage of having only an inchoate slit is that it prevents backbleeding out of the guidewire removing means 46 during performance of the angioplasty procedure. It is possible, however, to have the guidewire removing means be formed from an inchoate slit in only the portion of the guidewire exposed to the patient's vasculature. The remainder of the guidewire removing means 46 that is inside the patient and inside the guiding catheter can be a fully formed slit or a perforated slit without creating backbleeding problems.

Figure 4:
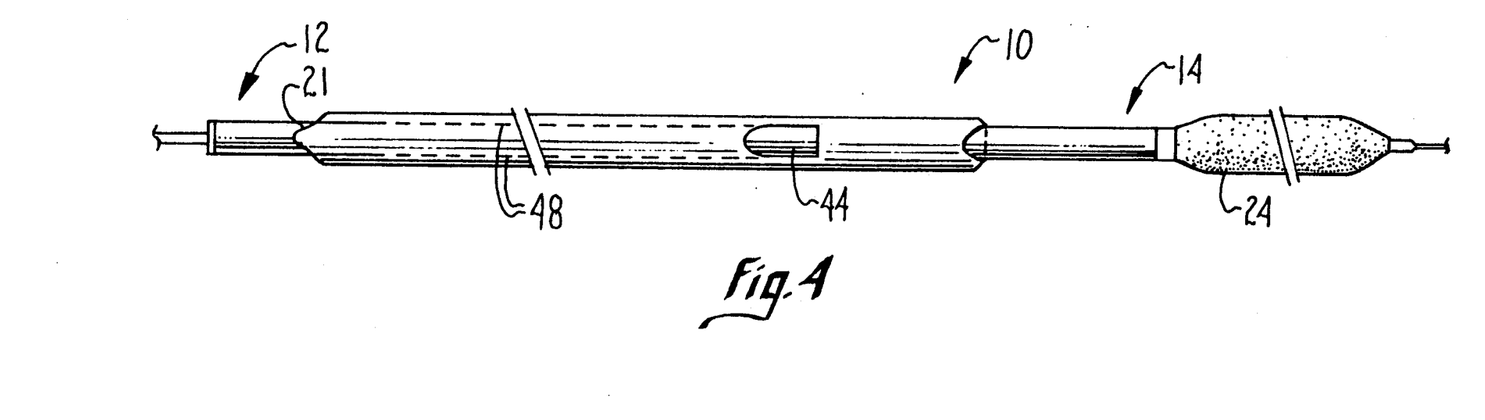
FIG. 4 is an on-face ventral view of one embodiment of the present bailout catheter incorporating a distal side port and longitudinal guidewire removing means formed by parallel slits.

The guidewire removing means 46 is also contemplated to include other conformations, such as a removable tear strip 47 defined by a pair of parallel weakened lines 48 extending distally from the proximal opening 21, as shown in FIG. 4. In a preferred embodiment, the lines 48 at the very proximal end of the tear strip 47 are severed to form a tab. Pulling on the tab then removes the remainder of the tear strip 47 by severing the weakened areas 48.

Figure 5:
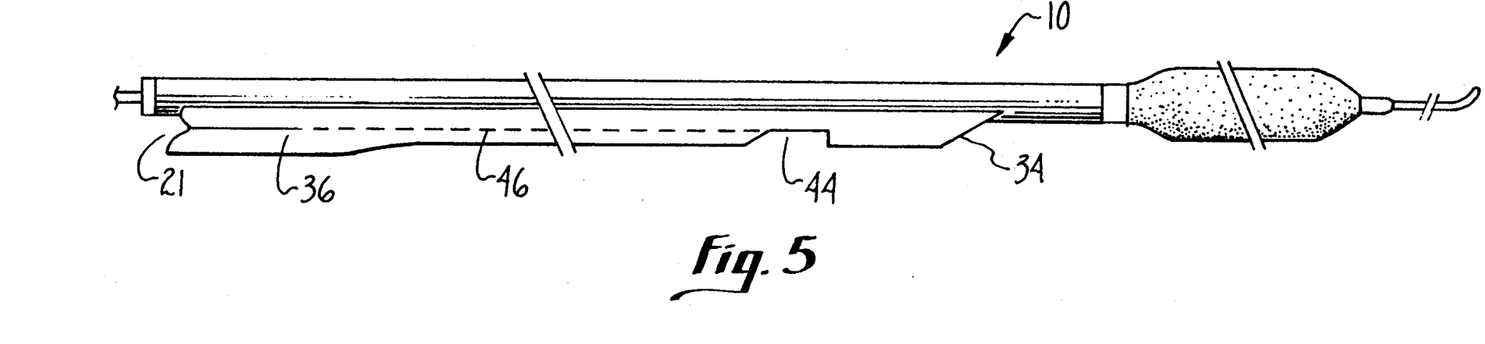
FIG. 5 is an external profile view of the catheter of FIG. 4.

FIG. 5 reveals a profile view of the embodiment of FIG. 4 wherein the guidewire removing means 46 comprises a tear away strip extending distally from the proximal opening 21 to the side port 44.

The guidewire removing means 46 normally extends from the proximal opening 21 (normally outside the patient) distally along the length of the bailout lumen 20 to a point that is ordinarily inside the patient when the catheter 10 is properly placed for performance of an angioplasty procedure (FIGS. 3, 4, 5). Thus, the guidewire removing means begins at a point ordinarily outside the patient and outside the guiding catheter upon proper placement of the catheter 10 and extends distally to a point ordinarily inside the patient upon such placement. Advantageously, the guidewire removing means 46 extends at least 50% of the length of the catheter shaft 11. From another perspective, the guidewire removing means 46 extends distally for at least 40 cm, preferably at least 60 or 70 cm, and more preferably at least 80, 90 or 100 cm. In one embodiment, the guidewire removing means can extend the entire length of the bailout lumen 20.

The guidewire removing means 46 may advantageously extend distally to the side port 44, and in one embodiment of the invention, may extend an additional distance distally beyond the side port 44. The guidewire removing means 46 preferably terminates proximally of the balloon 24, and may be immediately adjacent the balloon 24, at the distal end of the bailout lumen 20, or may be 2 cm, 5 cm, 10 cm, 20 cm, 30 cm, or more proximally of the balloon 24.

If the guidewire removing means 46 is not a slit prior to its use, it can become a slit or opening during its use. At the distal end of the removing means 46, the distal side port 44 can be used as the alternate entry point for the guidewire into the bailout lumen 20, especially for rapid back-loading in a catheter exchange.

The ability to remove the guidewire from almost the entire length of the bailout lumen 20 is important in catheter removal. In embodiments of the invention lacking a guidewire removing means 46, a guidewire extension must be attached to the proximal portion of the guidewire 33 to allow complete catheter removal from the patient. However, by laterally removing the guidewire 33 through the removal means 46, the catheter 10 can be retracted from the patient without an exterior guidewire extension.

The particular method of using the guidewire removing means is as follows. When the guidewire is to be removed radially or laterally out of the bailout lumen 20, the guidewire removing means 46 provides a slit or opening in the outside wall 36 of the bailout lumen 20 through which the guidewire 33 may be removed from the bailout lumen 20. This slit or opening, if not fully formed, may be completed by cutting the outside wall 36 of the bailout lumen 20, by tearing or rupturing a weakened area in the outside wall 36, or by tearing loose a removable strip. In a preferred embodiment the guidewire removing means 46 is a weakened area that is fully opened only after the guidewire 33 is removed through the guidewire removing means 46.

In one embodiment, the guidewire 33 simply tears open a slit through the outside wall 36 of the bailout lumen 20. Alternatively the outside wall 36 may be provided with a filament in association with the guidewire removing means 46. The filament may be a continuous fiber or strand extending along the length of the guidewire removing means and inside at least a portion of the outside wall 36 of the guidewire lumen 20. When the filament is pulled outwardly, it tears a slit into the outside wall 36 of the bailout lumen 20. It preferably begins either at the proximal end of the catheter 10 or within 5, 10, or 15 cm of the proximal end.

Preferably, once the slit is formed the guidewire is removed by securely holding the guidewire in position while pulling the catheter out of the patient. This results in the catheter being pulled off of the stationary guidewire as the catheter is removed from the patient.

The catheter of the present invention may be used as a rapid exchange catheter with the guidewire 33 extending through the side port 44 and out of the distal end 34 of the bailout lumen 20. Alternatively, it may be used as a conventional over the wire catheter with the guidewire 33 extending substantially the entire length of the catheter shaft 11 from the proximal end 21 longitudinally through the entire length of the bailout lumen 20 and out of the distal end 34 thereof.

Figure 6:
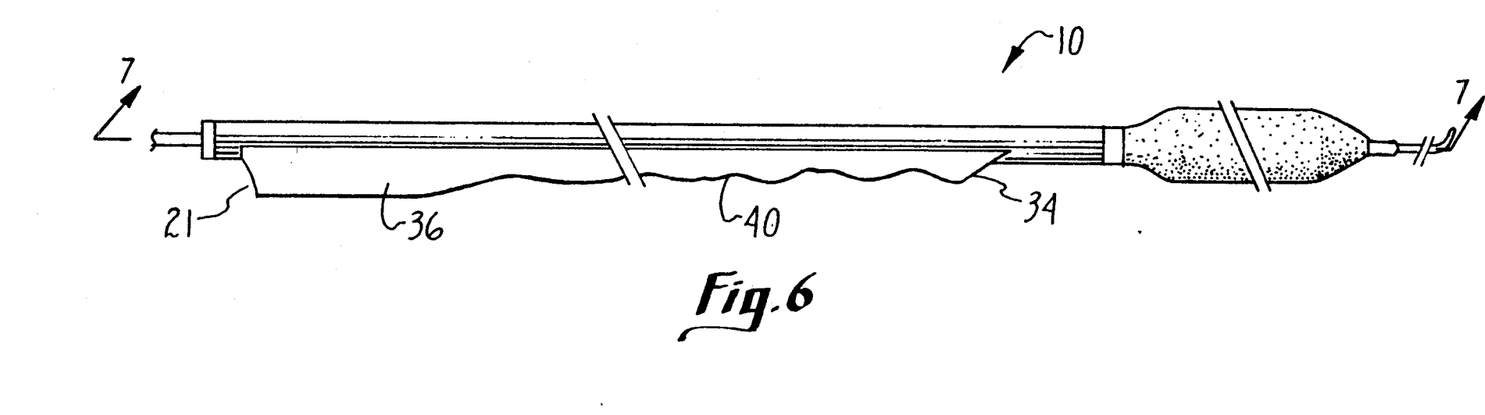
FIG. 6 is an external profile view of one embodiment of the present bailout catheter incorporating a collapsible guidewire lumen.

In order for the distal end of the catheter 10 to be the smallest possible diameter, the outer shell of the bailout lumen 20 is optionally separated into the proximal thicker-walled portion 36 and a thinner-walled, collapsible, more distal portion 40 (FIG. 6). The thin-walled distal portion 40 can begin immediately distal (e.g., within 2 to 20 cm) of the proximal opening 21 of the guidewire lumen and continue longitudinally to the guidewire distal opening 34. Alternatively, the thin walled distal portion 40 can continue to a point well inside the patient during use of the catheter 10, or to a point just inside the guiding catheter. During advancement of the catheter 10 through the patient's vasculature, the thin-walled portion 40 of the bailout lumen 20 can collapse, thereby decreasing the overall circumference of the catheter's most distal portion. The more proximal portion of the guidewire wall 36 is preferably thicker, thereby allowing a guidewire removing means (not shown) to be maintained by polymer memory. A thicker guidewire wall 36 also facilitates the pushability characteristics of the catheter shaft.

Figure 7:
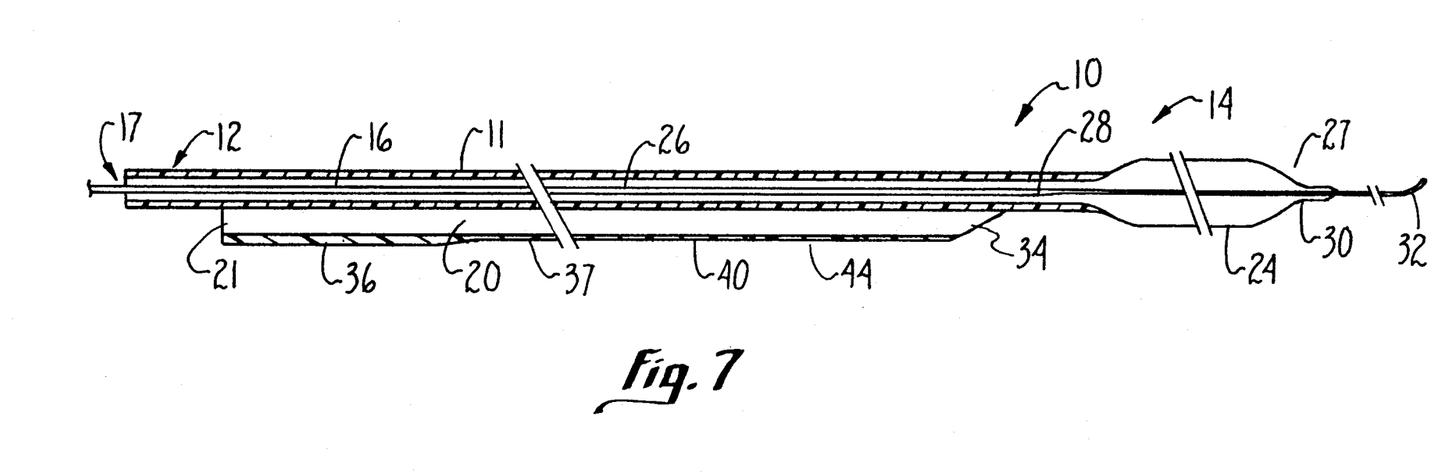
FIG. 7 is a longitudinal cross-section of the fixed wire balloon catheter of FIG. 6, taken along the line 7—7.
Figure 8:
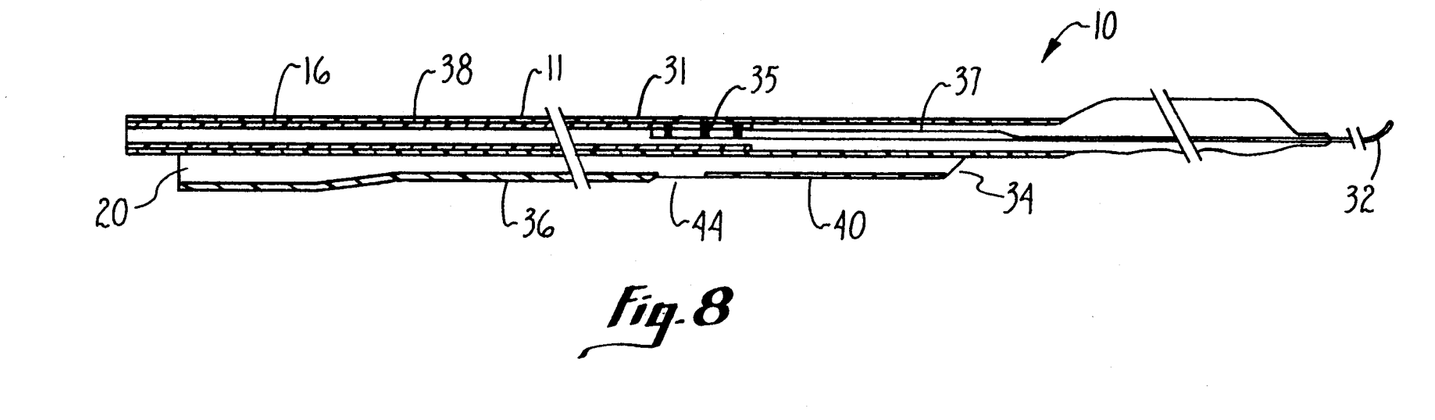
FIG. 8 is a longitudinal cross-section of a fixed wire balloon catheter incorporating a hypotube and a distal side port.

As shown in FIG. 7, the thin-walled portion 40 of the bailout lumen 20 can extend from a point proximal to the side port 44 to a point distal to, and including the side port 44. Other embodiments of the thin wall 40, as illustrated in FIG. 8, include the thin wall being located only distal to side port 44 and continuing to the distal end of the bailout lumen 20.

FIG. 7 is a longitudinal cross-section cut along the line 6—6 of FIG. 6. The catheter 10 includes a balloon inflation lumen 16 extending distally through the catheter shaft 11, terminating distally at the distal end 14 of the catheter shaft 11 and in fluid connection with the balloon 24. Furthermore, FIG. 7 also illustrates the bailout lumen 20 running distally, at or about the proximal end 12 of the catheter shaft 11, along the catheter shaft 11, to a point somewhat proximal of the distal end 14 of the catheter shaft 11.

Fluid introduced into the proximal end 17 of the balloon inflation lumen 16 can travel distally through the catheter shaft 11 to inflate the angioplasty balloon 24. The bailout lumen 20 terminates approximately 1 cm to 10 cm, more preferably from 2 cm to 6 cm of the proximal end of balloon 24.

Longitudinally traversing the interior portion of the balloon inflation lumen 16 and balloon lumen 22 is a steerable torquewire 26 (FIG. 7). The torquewire 26 is preferably of a small enough diameter such that fluid introduced at the proximal opening 17 of the balloon inflation lumen 16 can pass around the torquewire 26 distally and flow into the balloon 24 without impediment. The torquewire 26 is preferably made of flexible metal material, such as stainless steel.

The torquewire 26 is permanently affixed to the distal end 27 of the balloon 24 at a connection point 30. In one preferable embodiment of the current invention, the torquewire 26 may be reduced in diameter at a torquewire reduction point 28. This reduction point 28 is normally located at the point where the balloon 24 and balloon inflation lumen 16 intersect. At the torquewire diameter reduction point 28, the torquewire 26 diameter can be reduced by up to 50 percent. Other embodiments having greater or lesser reductions or no reduction in torquewire diameter are also contemplated within the present invention.

The torquewire 26, which is directly connected to a distal floppy tip 32 is used by the operator to steer the catheter 10 through the patient's vasculature.

Attachment of the torquewire 26 to the balloon 24 at the distal connecting point 30 provides a means of steering the catheter 10 and the leading catheter tip 32. For example, clockwise rotation of the torquewire 26 correspondingly leads to a clockwise rotation of the catheter 10 and the tip 32. The torquewire 26 thereby provides a steerage means of the catheter 10 through the patient's vasculature.

The torquewire tip 32 defines the distal-most end of the catheter device 10 protruding a distance of between 1.0 cm and 3.0 cm from the connecting point 30. The torquewire tip 32 may be of conventional guidewire design, and is preferably shapeable by the physician.

Other variations of the fixed wire bailout catheter are also contemplated, such as the alternative design detailed in FIG. 8. In this embodiment of the present invention, a non-bioactive metal such as a stainless steel hypotube 31 forms at least a portion of the catheter shaft proximally of the balloon, and defines the balloon inflation lumen 16. The hypotube 31 preferably extends from the proximal end of the catheter 10 distally to a point preferably about 10 cm to 30 cm proximal to the balloon 24. The distal end of the hypotube 31 may be affixed to a shortened torquewire 37 at a point 35 in the interior of the catheter shaft 11. An operator's rotational movement of the hypotube 31 thereby causes rotation of both the catheter shaft 11 and truncated torquewire 37 providing a steerage means for the catheter 10. The hypotube 31 may advantageously be coated with a polymer material 38 to facilitate bonding between the bailout lumen and the catheter shaft.

The hypotube 31 imparts stiffness to the catheter 10, providing enhanced pushability and decreasing the tendency of the catheter shaft 11 to buckle.

Once the angioplasty procedure has been performed, by inflating the balloon 24 through fluid injection into the balloon inflation lumen 16, it sometimes becomes necessary to exchange the catheter 10 for an alternate catheter. This exchange may be necessary because the original balloon was an incorrect size for suitable performance of the angioplasty procedure, or an emergency situation, such as vascular collapse, may require the insertion of a perfusion catheter.

It would be advantageous therefore to provide a rerouting means such as a guidewire so that the new catheter could be securely and safely inserted back to the original stenotic area of the patient's vasculature. Such a mechanism is provided by the fixed wire angioplasty catheter of the present device.

Currently available fixed wire catheters have no inherent bailout provision. These devices require complete removal and re-routing of the catheter if an exchange becomes necessary. Such a re-route is usually under emergency conditions. These maneuvers may cause danger and risk to the patient since reinsertion of a balloon or perfusion catheter may not be possible during such an emergency due to obliteration or occlusion of the vessel channel. Either procedure increases the risk to a patient by taking extra time in an emergency.

Figure 9:
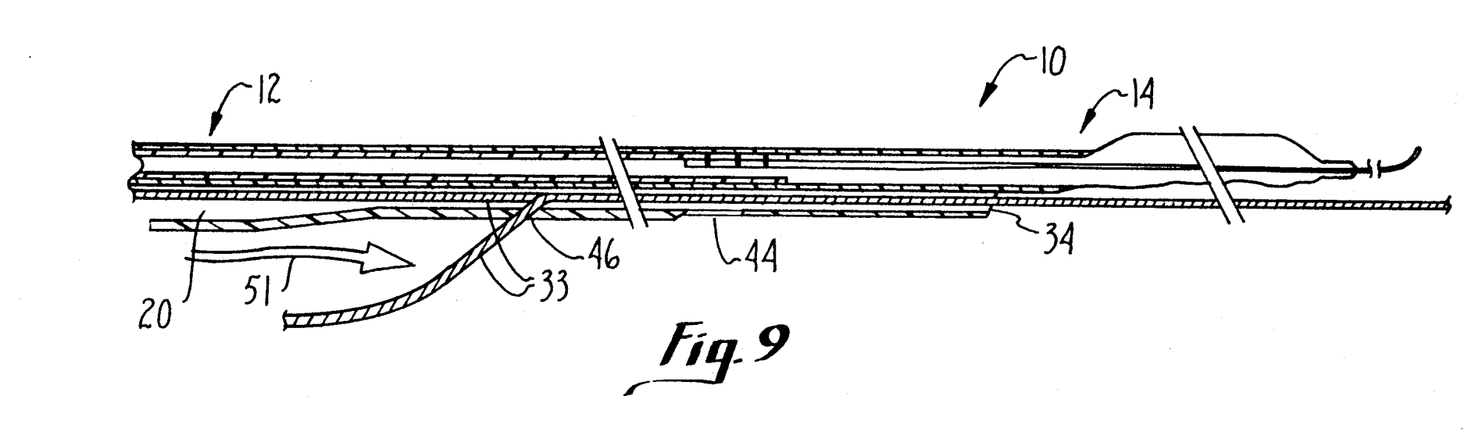
FIG. 9 is a longitudinal cross section of the fixed wire balloon catheter of FIG. 8, showing lateral movement of a guidewire out of a bailout lumen for rapid exchange function.

Referring now to FIG. 9, before removing the original catheter 10, one method of using the present device comprises inserting a guidewire 33 into the bailout lumen 20 until it protrudes from a guidewire distal opening 34 and is aligned in parallel with the tip of the torquewire 32. With the guidewire now in place inside the bailout lumen 20, the catheter 10 can be retracted from the vasculature and patient while the guidewire 33 remains in its position in the patient. A new catheter can then be slid distally over the guidewire 33, advancing to the same place as the original catheter 10.

Another aspect of the present invention catheter is a low profile catheter which inherently may readily and rapidly be converted from one mode of use to the other. Thus, the catheter can be used first as a rapid exchange catheter, with the guidewire extending in the bailout lumen 20 only from the side port 44 to the distal end of the catheter 34. It can then be converted from this rapid exchange mode of use to conventional over-the-wire use simply by removing the guidewire and, while maintaining the catheter 10 in place in the patient, inserting a new guidewire 33 into the proximal end 21 of the bailout lumen 20 and extending the guidewire 33 out of the distal end 34 of the catheter.

Figure 10:
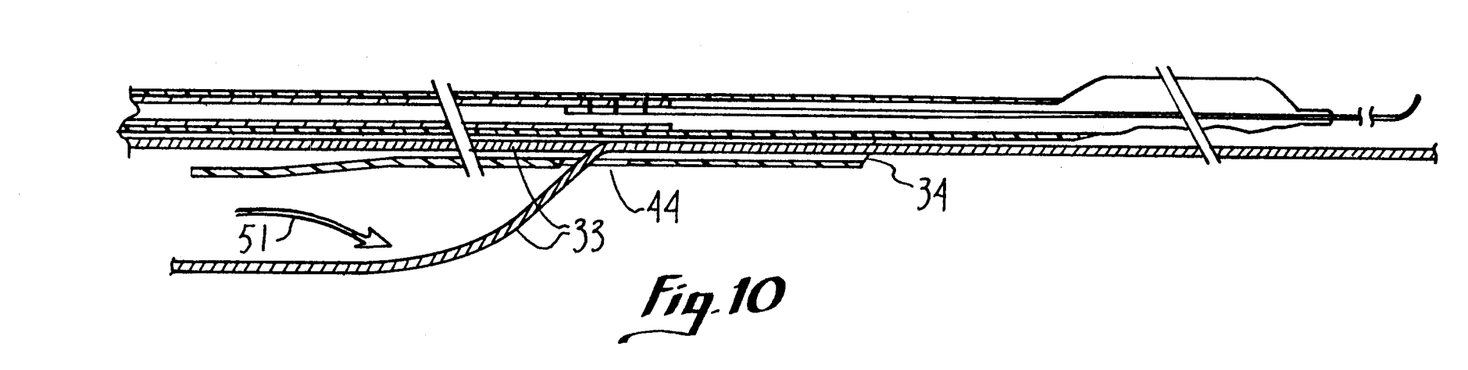
FIG. 10 is a longitudinal cross section of the fixed wire balloon catheter of FIG. 9 showing a completed lateral guidewire transfer.

With a guidewire 33 extending the entire length of the bailout lumen 20, the catheter can be removed and reinserted as a rapid exchange catheter. With the guidewire 33 extending proximally out of the proximal opening 21, the guidewire 33 is maintained in position in the patient while the guidewire is moved laterally out of the outside wall 36 of the bailout lumen 20 through the guidewire removing means 46 in the direction indicated by arrow 51 (FIGS. 9 and 10). The catheter 10 is pulled back proximally until the distal end 14 of the catheter 10 is outside of the patient. During this portion of the procedure, the guidewire 33 is held stationary by grasping it at the proximal end. Then the operator may hold the guidewire 33 by grasping the portion of the guidewire 33 exposed at the distal end 14 of the catheter 10, remove the catheter 10 off of the proximal end of the guidewire 33, and insert a new catheter of any type over the guidewire 33 while maintaining the position of the tip of guidewire 33 in the patient's vascular system. The insertion of the new catheter 10 may be accomplished in rapid exchange mode by retrograde insertion of the proximal end of the guidewire 33 through the distal end 34 of the bailout lumen 20 and out of the side port 44. The proximal end of the guidewire is then held in position while the catheter 10 is advanced forward into the patient.

Alternatively, if desired, the guidewire 33 may be removed with the catheter maintained in position, and in a matter of seconds the guidewire may be reinserted through the proximal opening 21 of the catheter shaft 11 to convert back to bailout function.

Thus, it will be appreciated that the low profile fixed wire catheter of the present invention can easily be used in either a rapid exchange mode or an over the wire mode; that conversion between modes of use may be readily accomplished; that guidewire exchange may be accomplished in either mode of use, and that catheter exchange when in either mode of use can be accomplished without use of an extension guidewire; and that all of the forgoing conversions and modes of use can be accomplished while maintaining the positioning of either the guidewire or the catheter in the patient.

Thus, one method of the present invention comprises inserting the guidewire 33 through the bailout lumen 20 of the catheter illustrated in FIG. 9, (which is already in place in a patient) with the guidewire 33 passing through the proximal opening 21 (FIG. 3) of the bailout lumen 20 and extending from that point distally through the bailout lumen and out of the distal end 34 thereof. The guidewire 33 can then be exchanged by removing it and reinserting it through the proximal opening 21.

The catheter can be exchanged by holding the guidewire stationary as explained above while the catheter is being withdrawn so that the guidewire 33 is pulled through the guidewire removing means 46 until the distal end of the catheter is outside the patient. Specifically, as shown in FIGS. 9 and 10, a guidewire 33 is first inserted into the empty bailout lumen 20 and advanced distally until reaching and traversing the distal end 34 of the bailout lumen 20. Referring to FIG. 9, while the catheter 10 is being removed from the patient, the guidewire 33 is pulled laterally, in the direction indicated by the arrow 51, through the guidewire removing means 46. As the catheter 10 emerges from the guiding catheter and patient, the guidewire 33 transits laterally through the guidewire removing means 46 thereby negating the need for an exterior guidewire extension. Referring to FIG. 10, the guidewire 33 can thereafter be laterally removed from the guidewire removing means 46 in the bailout lumen 20 even further until reaching the side port 44.

The guidewire 33 is then held distally of the catheter and a new catheter is inserted, this time in rapid exchange mode. Once the new catheter is in place, the guidewire can be removed or can be exchanged (if desired) to convert the catheter back into the over-the-wire mode of use as explained above.

Angioplasty Methods

Figure 11A:
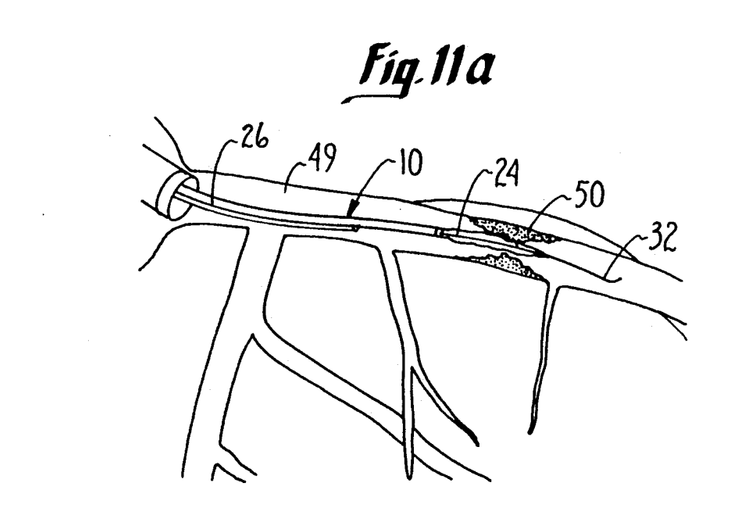
Figure 11B:
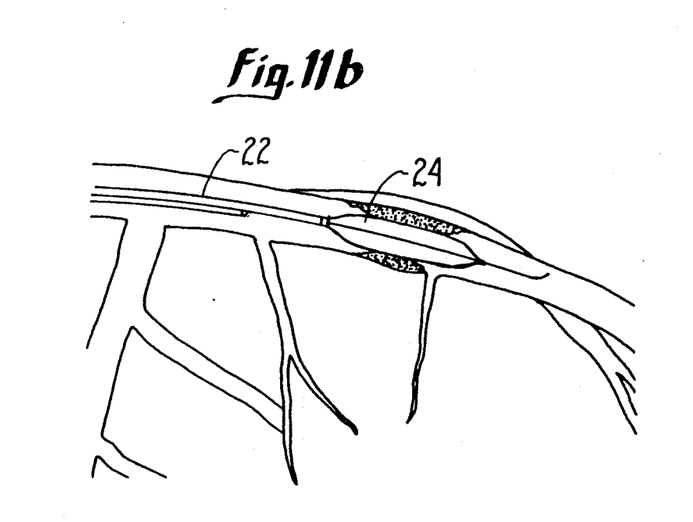

Referring to FIG. 11, a set of four panels labeled FIGS. 11a, 11b, 11c and 11d sequentially illustrate one clinical scenario using the fixed-wire/bail-out angioplasty catheter 10. In FIG. 11a, the deflated balloon 24 of the catheter 10 is inserted into a stenotic area 50 of a patient's vasculature 49. The catheter 10 is steered to the patient's stenotic region by manipulating the torquewire tip 32. Once the balloon 24 is positioned in the vessel at the stenotic lesion 50, it is inflated by a fluid media as illustrated in FIG. 11b.

Figure 11C:
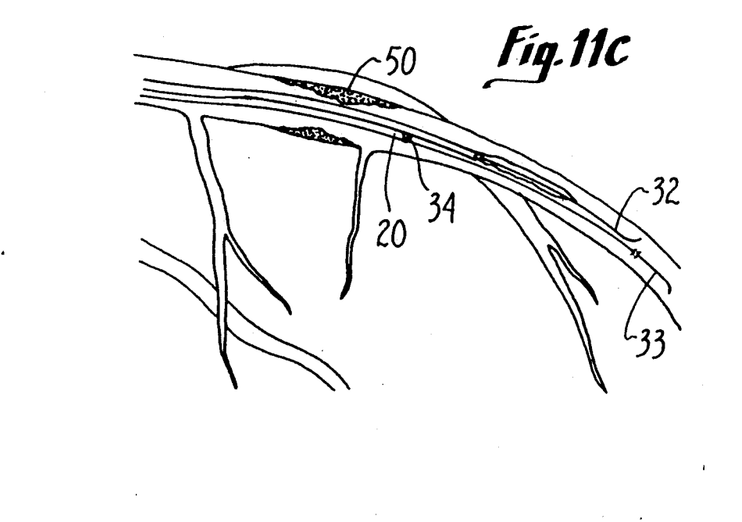
Figure 11D:
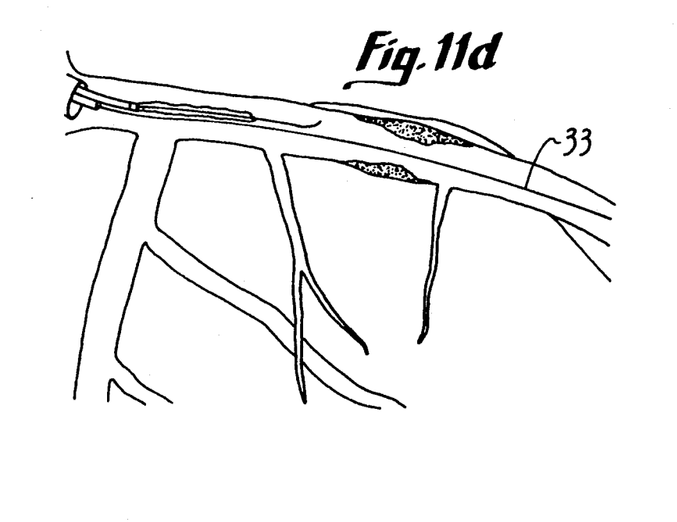
Figure 12A:
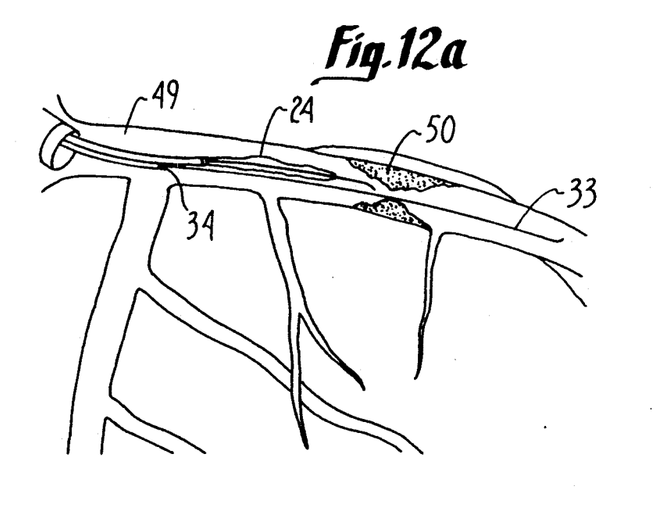
Figure 12B:
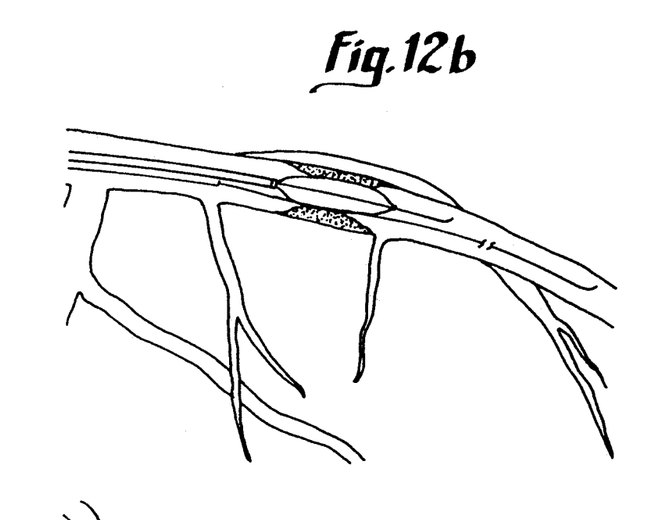
Figure 12C:
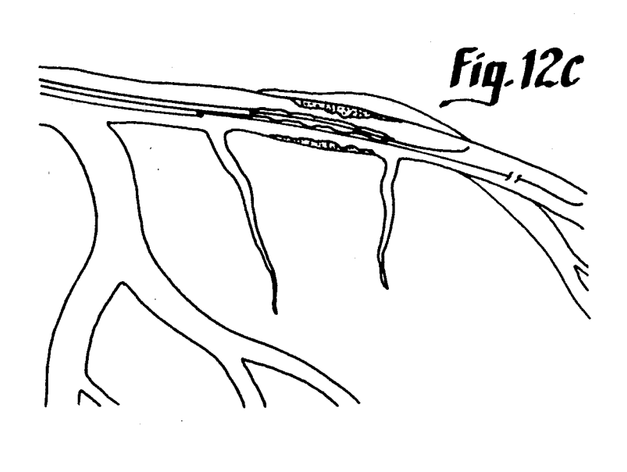
Figure 12D:
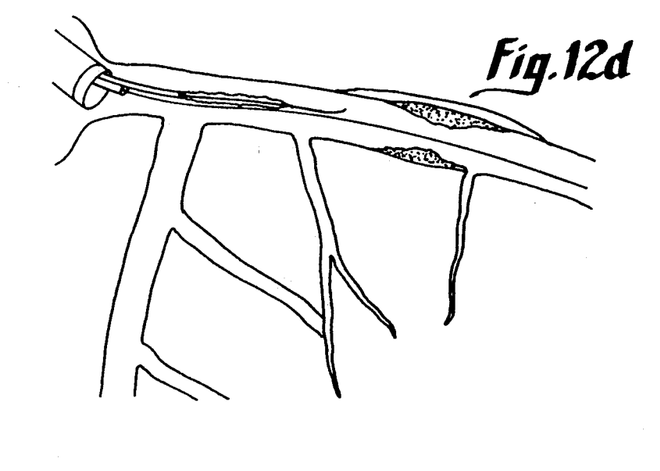

The balloon 24 is then deflated and advanced distally past the stenotic lesion 50 (FIG. 11c) so that the distal guidewire lumen 34 is past the lesion previously dilated. At this point a guidewire 33 is inserted into the bailout lumen 20 and advanced distally until it emerges from the distal guidewire opening 34. The guidewire 33 is then advanced further distally until it extends in parallel to the catheter tip 32 of the torquewire 26. Once the guidewire 33 is aligned or distal to the torquewire tip 32, the fixed-wire catheter 10 can be removed from the patient leaving the guidewire 33 in place (FIG. 11d). Once the balloon catheter has been completely removed from the patient, the physician has the option of reinserting another catheter over the guidewire 33 into the stenosis as part of a bailout procedure.

Figure 13A:
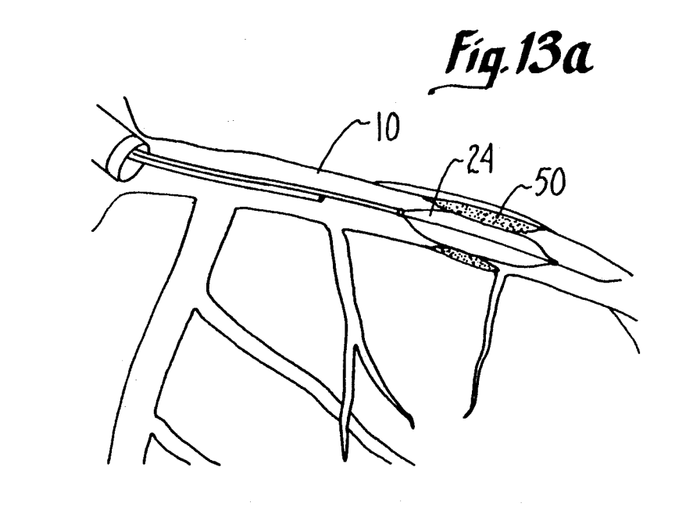
Figure 13B:
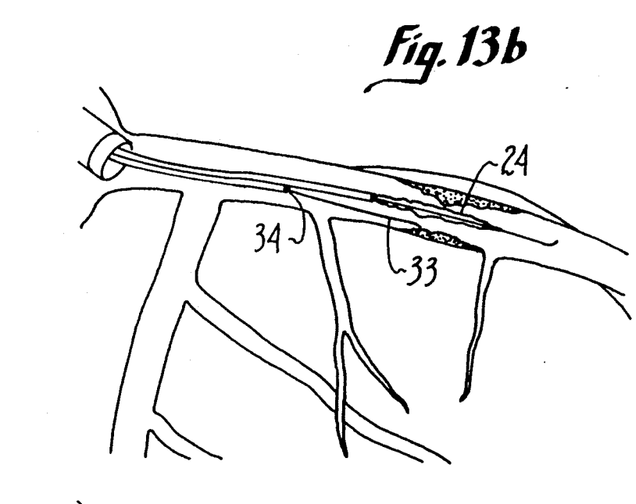

FIG. 12 describes a second clinical scenario illustrated by panels E, F, G, and H. In FIG. 12 the catheter 10, having an angioplasty balloon 24, is first positioned at a point immediately proximal to the stenotic lesion 50 (FIG. 12a). The guidewire 33 is then advanced through the bailout lumen 20 distally until it emerges from the distal opening 34. The guidewire 33, with its tip out of the catheter 20 but inside the vessel 49 is then advanced further passing through and beyond the stenotic lesion 50. The catheter 10 is then steered over the in-place guidewire 33 distally so that the balloon 24 is positioned inside the lesion 50 (FIG. 13a). A fluid can then be injected into the balloon inflation lumen 16 inflating the balloon 24 and dilating lesion 50. The balloon can preferably be inflated and deflated repeatedly, allowing blood flow between cycles, until the lesion is fully dilated. After dilation, the balloon 24 is deflated (FIG. 12c) by withdrawing the fluid from the balloon inflation lumen 16, and the catheter 10 removed leaving the guidewire 33 in place so that another angioplasty catheter can be safely employed over the wire if necessary (FIG. 12d).

Figure 13C:
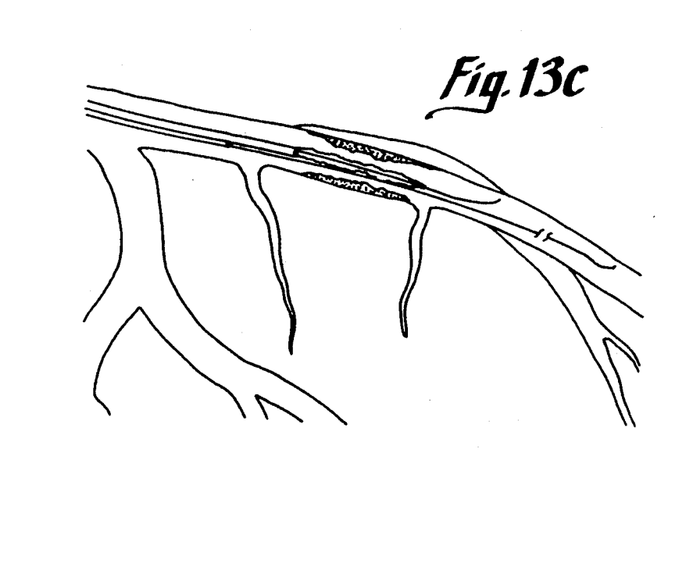
Figure 13D:
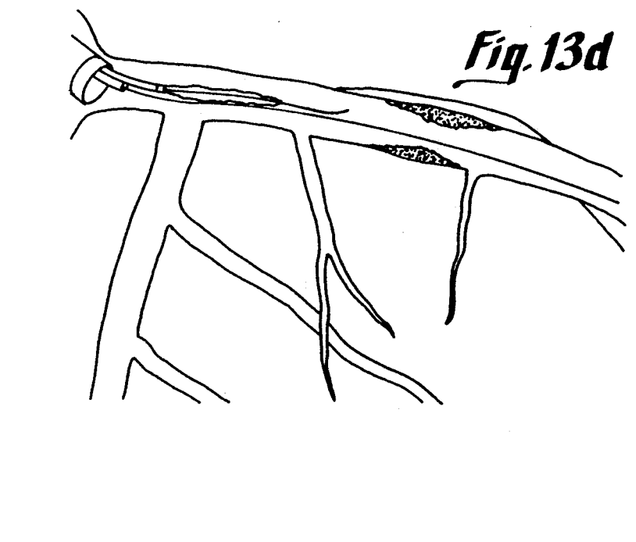

Another alternate clinical scenario is illustrated in FIGS. 13a, 13b, 13c, and 13d. In this scenario, the catheter 10 is inserted into a patient and moved distally into the stenosis 50. The stenotic lesion 50 is then dilated by inflation of the balloon 24 (FIG. 13a). After dilation, the balloon 24 is deflated and the guidewire 33 is inserted into the bailout lumen proximal opening 21 and advanced distally until it exits the distal opening 34 FIG. 13a. The guidewire 33 is then advanced further, through and beyond the just dilated lesion 50, while the deflated balloon 24 remains in place (FIG. 13c). After the guidewire 33 is positioned distal to the lesion 50 the balloon catheter 10 can be withdrawn leaving the guidewire 33 in place so that further angioplasty catheters can be easily inserted, if necessary (FIG. 13d).

Figure 14A:
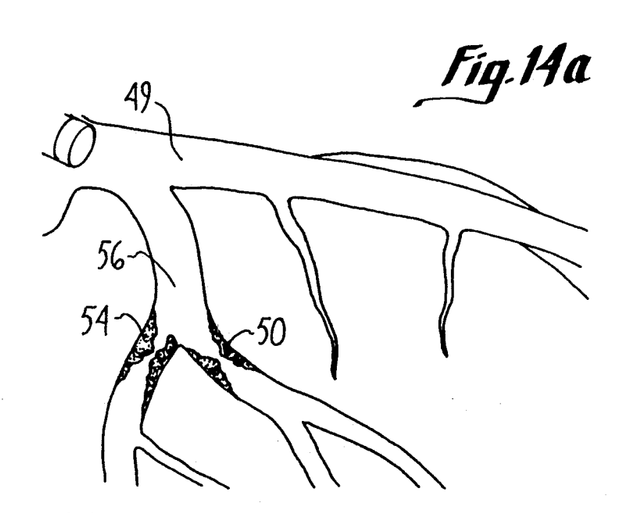
Figure 14B:
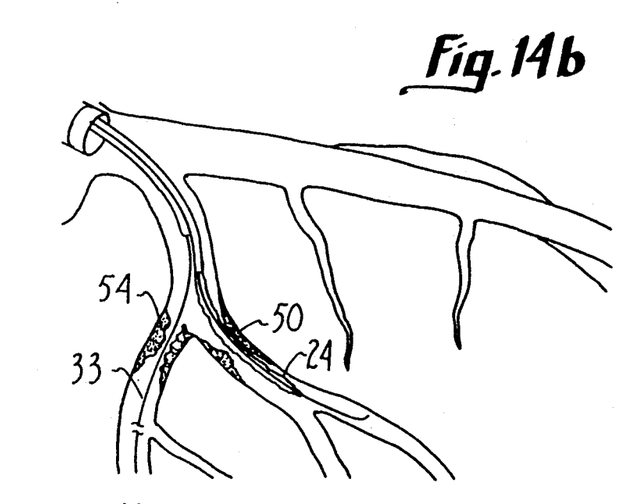
Figure 14C:
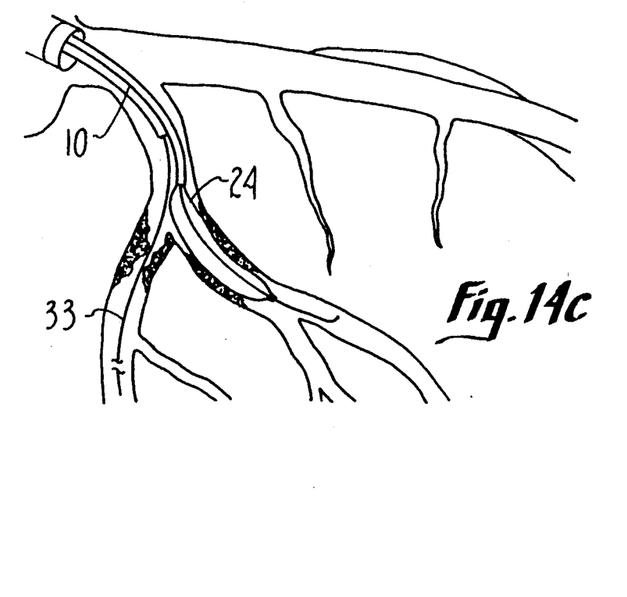
Figure 14D:
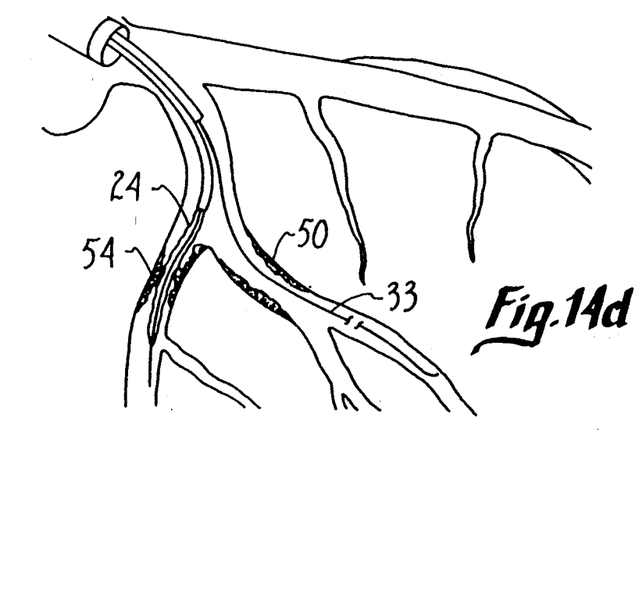
Figure 14E:
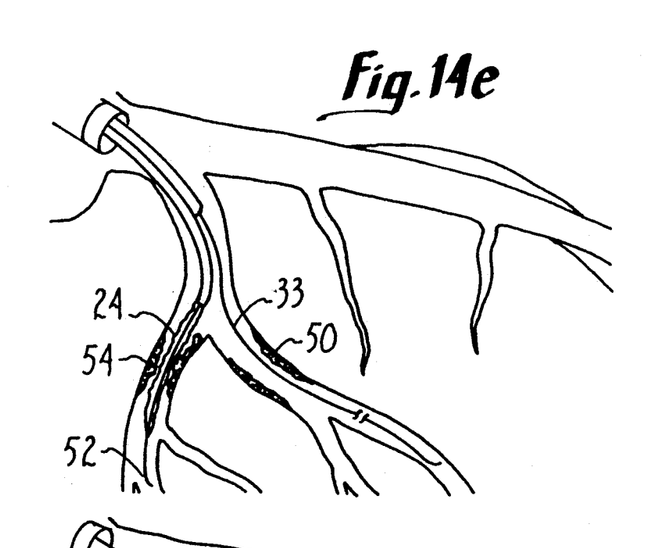
Figure 14F:
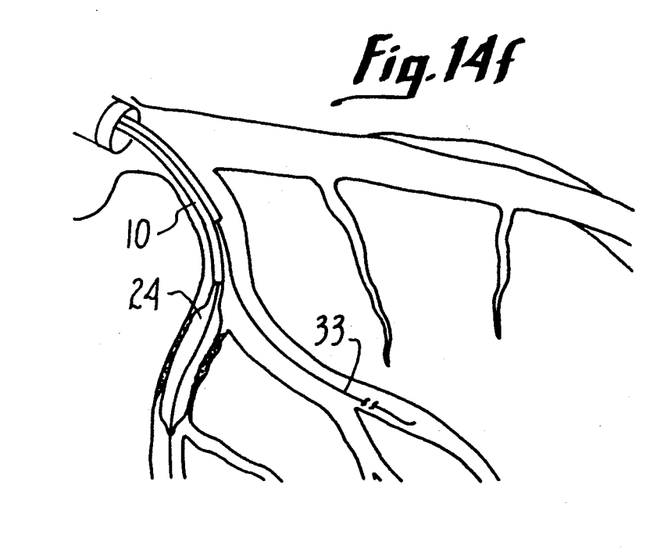
Figure 14G:
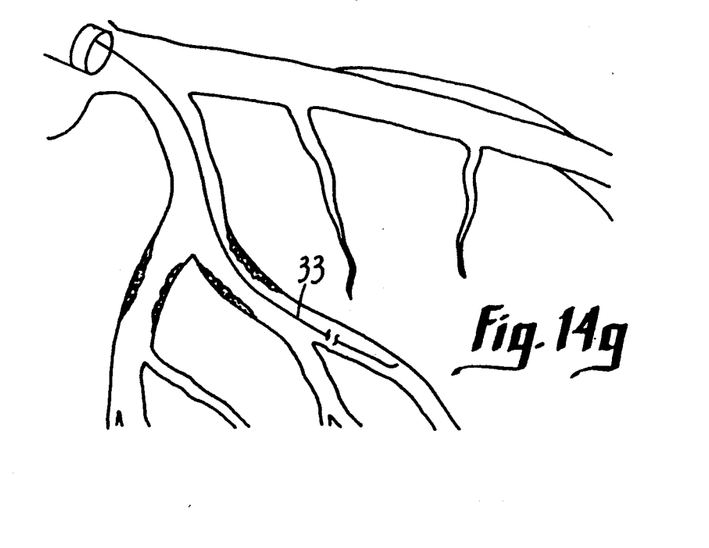

In some instances a patient's vasculature has more than one stenotic lesion. FIGS. 14a and 14h illustrate a double lesion of bifurcation at points 50, 54. In this case the patient has a vascular "Y" junction 56 at a point proximal to the lesions 50, 54. This patient therefore requires a double angioplasty procedure with balloon dilation at each stenotic lesion. The clinical scenario outlined in FIGS. 14a through 14h. In order to treat both lesions 50, 54 the fixed-wire catheter 10 is first placed at lesion 50 and the guidewire 33 is positioned passing through the second lesion 54 FIG. 14a. The first lesion 50 is then dilated by inflation of the balloon 24 (FIG. 14b). After dilation, the position of the guidewire 33 and balloon catheter 10 are switched bringing the balloon 24 in contact with the second lesion 54 and the guidewire 33 passing through the first lesion 50 FIGS. 14c and 14d. The balloon 24 is again inflated with fluid causing dilation of the second stenotic lesion 54 (FIGS. 14e). After completing dilation of the second lesion 54, the balloon catheter 10 can be removed leaving the guidewire 33 in place so that further angioplasty procedures can be carried out if necessary (FIGS. 14f).

Although particular preferred embodiments of the invention are emphasized above, the scope of the invention is not limited to those embodiments. Instead, it is intended that the invention extend to and include the full lawful scope of the following claims.

What is claimed is:

1. An angioplasty catheter, comprising:

a catheter shaft having a proximal end and a distal end, with a balloon inflation lumen extending therethrough;

a fixed, steerable torquewire extending through at least a portion of said shaft and out of the distal end thereof;

an angioplasty balloon on the distal end of said catheter operatively communicating with said balloon inflation lumen for inflation and deflation of said balloon, wherein the proximal end of said balloon is attached to the distal end of said catheter shaft and the distal end of said balloon is attached to said torquewire; and a bailout lumen having a proximal opening and a distal opening, said lumen extending along said catheter shaft from a point within about 30 cm of the proximal end of the catheter to a point proximal to and within about 30 cm of said balloon, said bailout lumen adapted to receive a removable guidewire and having an outer wall, said outer wall further comprising a side port extending therethrough, located between said proximal opening and said distal opening, said side port adapted to permit a guidewire to extend therethrough to pass through a distal portion of the bailout lumen.

2. The catheter of claim 1, wherein said outer wall is adapted to at least partially collapse into said bailout lumen when said bailout lumen is empty.

3. The catheter of claim 2, wherein only a distal portion of said outer wall of said bailout lumen is adapted to collapse when empty.

4. The catheter of claim 3, wherein a proximal portion of said outer wall is adapted to remain open when empty and is thicker than said collapsible distal portion thereof.

5. The catheter of claim 1, wherein said side port is located within about 30 cm of the distal end of said bailout lumen.

6. The catheter of claim 1, wherein said catheter further comprises guidewire removing means, adapted for removing a guidewire laterally out of said bailout lumen.

7. The catheter of claim 6, wherein said guidewire removing means is adapted to permit removal of a guidewire from the bailout lumen beginning at the proximal end of said bailout lumen and progressing distally to within no more than 30 cm of said balloon.

8. The catheter of claim 6, wherein said guidewire removing means comprises means for providing an opening through said outer wall extending longitudinally along said outer wall.

9. The catheter of claim 6, wherein said guidewire removing means comprises a slit extending longitudinally along at least 50% of the length of said outer wall.

10. The catheter of claim 6, wherein said guidewire removing means comprises a weakened area adapted to open into a slit extending longitudinally along at least 50% of the length of said outer wall.

11. The catheter of claim 10, wherein said outer wall has an open slit extending distally from the proximal end thereof to said weakened area.

12. The catheter of claim 6, wherein said guidewire removing means comprises a tear away strip forming at least a portion of said outer wall and adapted to tear away from said catheter and form an opening extending longitudinally along at least 50% of the length of said outer wall.

13. The catheter of claim 12, wherein said tear away strip is defined by two longitudinally extending parallel weakened areas of said outer wall.

14. The catheter of claim 13, wherein said tear away strip is further defined by two parallel formed slits extending from the proximal end of said outer wall to said weakened areas.

15. The catheter of claim 13, wherein said outer wall is joined to said catheter shaft along two longitudinally-extending junctions, and said weakened areas comprise said junctions.

16. The catheter of claim 6, wherein said guidewire removing means extends distally from the proximal opening of the bailout lumen along said outer wall to said side port.

17. A method for performing bailout of a fixed wire angioplasty catheter, comprising:
(a) advancing a first balloon catheter as defined in claim 1 into a patient's vascular system, wherein said vascular system includes a stenosis;
(b) advancing a guidewire through the bailout lumen of said first catheter and out of the distal end of said bailout lumen into a position in said patient's vascular system;
(c) removing said first balloon catheter from said patient while maintaining said guidewire in said position in the vascular system; and
(d) inserting a proximal end of the guidewire into the distal end of the bailout lumen of a second balloon catheter as defined in claim 1, such that said guidewire extends through a distal portion of the lumen and out through the side port and advancing the second catheter into the vascular system of said patient.

18. The method of claim 17, further comprising the steps, after step (a) and before step (b), of:
inflating and deflating the balloon of said first catheter in said stenosis; then
advancing said first catheter forward until the distal end of the bailout lumen is advanced to or through said stenosis;
whereby step (b) results in said guidewire extending into said stenosis.

19. The method of claim 17, wherein said guidewire is advanced into or through said stenosis in step (b), further comprising the step, after step (a) but before step (c), of:
inflating and deflating the angioplasty balloon of said first catheter in said stenosis with said guidewire extending through said stenosis.

20. The method of claim 17, wherein the angioplasty balloon of said first balloon catheter is inflated and deflated in said stenosis prior to step (b), and the guidewire is advanced past the deflated balloon in the stenosis in step (b).

21. A method for performing balloon angioplasty, in bifurcation lesions, comprising:
(a) advancing the balloon segment of a catheter as defined in claim into a first stenosis of the bifurcation in a patient's vascular system;
(b) advancing a guidewire through the bailout lumen of said catheter and out of the distal end of the bailout lumen into a second stenosis of the bifurcation in said patient; and
(c) inflating and deflating the balloon in said first stenosis.

22. The method of claim 21, further comprising the subsequent steps of:

(d) inserting the balloon into the second stenosis and the guidewire into the first stenosis; and (e) inflating and deflating the balloon in the second stenosis.

23. The method of claim 22, further comprising the subsequent step of:

removing said first balloon catheter over said guidewire, and inserting a second catheter into the vessel over said guidewire.

24. A method for performing bailout of a fixed wire angioplasty catheter, comprising:

(a) inserting a proximal end of a guidewire into the distal end of the bailout lumen of a first balloon catheter as defined in claim 1, said guidewire already in place at a stenosis in a patient's vascular system such that said guidewire extends through a distal portion of the lumen and out through the side port and advancing the first balloon catheter into a patient's vascular system;

(b) advancing the first balloon catheter into the stenosis and inflating and deflating the balloon to dilate said stenosis while said guidewire is in position in said stenosis; and (d) removing said first balloon catheter from said patient while maintaining said guidewire in position in said stenosis.

25. The method of claim 24, further comprising the following step:

(e) advancing a second catheter into the vascular system of said patient over said guidewire.

26. An angioplasty catheter, comprising:

a catheter shaft having a proximal end, a proximal portion, and a distal end, with a balloon inflation lumen extending therethrough;

a fixed, steerable torquewire extending through at least a portion of said shaft and out of the distal end thereof;

an angioplasty balloon on the distal end of said catheter operatively communicating with said balloon inflation lumen for inflation and deflation of said balloon, wherein the proximal end of said balloon is attached to the distal end of said catheter shaft and the distal end of said balloon is attached to said torquewire; and a bailout lumen extending along said catheter shaft from a point within about 30 cm of the proximal end of the catheter to a point proximal to and within about 30 cm of said balloon, said bailout lumen adapted to receive a removable guidewire, said bailout lumen having an outer wall, further comprising guidewire removing means in the outer wall of the bailout lumen, said guidewire removing means being adapted to permit a guidewire, extending through the bailout lumen, to be removed laterally through the outer wall.

27. A method for performing bailout of a fixed wire angioplasty catheter, comprising:

(a) advancing a first balloon catheter as defined in claim 26 into a patient's vascular system, wherein said vascular system includes a stenosis;

(b) advancing a guidewire through the bailout lumen of said first catheter and out of the distal end of said bailout lumen into a position in a stenosis in said patient's vascular system;

(c) advancing the first balloon catheter into the stenosis and inflating and deflating the balloon to dilate said stenosis while said guidewire is in position in said stenosis; and (d) removing said first balloon catheter from said patient by laterally removing the guidewire through the guidewire removing means in the bailout lumen while maintaining said guidewire in position in said stenosis.

28. The method of claim 27, further comprising the following step:

(e) providing a second balloon catheter as defined in claim 1;

(f) inserting a proximal end of the guidewire into the distal end of the bailout lumen, through the distal portion of the bailout lumen, and out through the side port; and (g) advancing the second catheter into the vascular system of said patient over said guidewire.

* * * * *